United States Patent [19]

Coleman et al.

[11] Patent Number: 4,612,287

[45] Date of Patent: Sep. 16, 1986

[54] **PLASMIDS CONTAINING A GENE CODING FOR A THERMOSTABLE PULLULANASE AND PULLULANASE-PRODUCING STRAINS OF *ESCHERICHIA COLI* AND *BACILLUS SUBTILIS* CONTAINING THE PLASMIDS**

[75] Inventors: Robert D. Coleman, Lisle; Michael P. McAlister, Willowbrook, both of Ill.

[73] Assignee: CPC International Inc., Englewood Cliffs, N.J.

[21] Appl. No.: 737,312

[22] Filed: May 23, 1985

[51] Int. Cl.[4] .................. C12N 15/00; C12N 9/44; C12N 1/20; C12R 1/125; C12R 1/19

[52] U.S. Cl. .................. 435/172.3; 435/210; 435/253; 435/320; 435/839; 435/849; 935/14; 935/29; 935/73; 935/74

[58] Field of Search ............ 435/320, 253, 210, 172.3

[56] References Cited

U.S. PATENT DOCUMENTS 4,493,893  1/1985  Mielenz et al. .................. 435/320
4,560,651  12/1985  Nielsen et al. .................. 435/95

*Primary Examiner*—Lionel M. Shapiro
*Attorney, Agent, or Firm*—Stanley M. Parmerter

[57] ABSTRACT

The gene coding for a thermostable pullulanase enzyme is incorporated into chimeric plasmids which are inserted into and reproduced by *E. coli* or *B. subtilis* host microorganisms. When microorganisms containing the chimeric plasmids are grown in fermentation media, they produce the pullulanase enzyme.

7 Claims, 3 Drawing Figures

PLASMIDS CONTAINING A GENE CODING FOR A THERMOSTABLE PULLULANASE AND PULLULANASE-PRODUCING STRAINS OF *ESCHERICHIA COLI* AND *BACILLUS SUBTILIS* CONTAINING THE PLASMIDS

FIELD OF THE INVENTION

This invention relates to chimeric plasmids which contain a gene coding for a thermostable pullulanase enzyme and to a process for their production. Cloning the gene into *Escherichia coli* (hereafter written *E. coli*) or *Bacillus subtilis* (hereafter written *B. subtilis*) and the use of the resulting microorganisms for production of a thermostable pullulanase enzyme are also described.

BACKGROUND OF THE INVENTION

A number of high molecular weight carbohydrates are polymers of glucose in which the glucose units are joined by either alpha-1,6-glucosidic linkages or alpha-1,4-glucosidic linkages. It is of considerable industrial importance to be able to cleave these linkages thereby breaking the large carbohydrate molecules into smaller molecules which are more useful in various applications. The breaking of the glucosidic linkages is frequently carried out by enzymes which are produced by microorganisms.

One group of enzymes known as alpha-amylases cleave the alpha-1,4-glucosidic linkages. The alpha-amylase enzymes are produced by such organisms as *Bacillus licheniformis* and *Bacillus stearothermophilus*. Such enzymes generally do not cleave the alpha-1,6-glucosidic linkages.

Another class of enzymes, sometimes referred to as glucoamylases, are capable of cleaving both alpha-1,6- and alpha-1,4-glucosidic linkages. These enzymes remove one glucose unit at a time from the nonreducing end of the large carbohydrate molecule. While they are capable of hydrolyzing certain alpha-1,6-glucosidic linkages, they hydrolyze the alpha-1,4-glucosidic linkages much more rapidly.

Other enzymes which hydrolyze certain alpha-1,6-linkages are classified as pullulanases. These enzymes are capable of hydrolyzing the alpha-1,6-linkages in the polysaccharide, pullulan, to give the trisaccharide, maltotriose. They do not hydrolyze the alpha-1,4-linkages in pullulan. The first pullulanase described was an extracellular enzyme produced by *Aerobacter aerogenes*. References to this enzyme and other enzymes capable of hydrolyzing alpha-1,6-linkages are given in U.S. Pat. Nos. 3,897,305 and 3,992,261. These enzymes are thermolabile and cannot be used at temperatures much above 50° C. A pullulanase enzyme produced by the bacterium, *Bacillus acidopullulyticus*, is described in British Patent 2,097,405. This pullulanase is sufficiently thermostable to be employed at 60° C. These enzymes, as well as all previously-known pullulanases, have been obtained from aerobic microorganisms.

Recently, it has been discovered that the anaerobic microorganism, *Thermoanaerobium brockii* (hereafter written *T. brockii*), produces a pullulanase enzyme with even greater thermostability. We have now isolated the gene coding for this thermostable pullulanase and inserted it into plasmid vectors. These vectors have in turn been incorporated into strains of *E. coli* and *B. subtilis*. The resulting genetically-engineered microorganisms produce the thermostable pullulanase when they are grown in suitable media.

SUMMARY OF THE INVENTION

In accordance with this invention, there is provided an essentially pure plasmid, having a genetic sequence coding for a thermostable pullulanase enzyme, selected from the group: pCPC901, having a molecular weight of approximately 15.3 kb and a restriction endonuclease cleavage map as shown in FIG. 1; pCPC902, having a molecular weight of approximately 9.9 kb and a restriction endonuclease cleavage map as shown in FIG. 2; and pCPC903, having a molecular weight of approximately 7.5 kb and a restriction endonuclease cleavage map as shown in FIG. 3.

Further, in accordance with this invention, there is provided a strain of *B. subtilis* containing the plasmid, pCPC903, capable of growing at a temperature of 37° C. for about 32 hours without loss of the plasmid, and capable of producing an extracellular thermostable pullulanase enzyme.

In addition, in accordance with this invention, there is provided a strain of *E. coli*, capable of growing in a medium containing ampicillin at a concentration of 100 $\mu$g/ml and containing a plasmid which includes a thermostable pullulanase coding gene, said plasmid selected from a group consisting of pCPC901 and pCPC902.

Finally, in accordance with this invention, there is provided a process for preparing a thermostable pullulanase enzyme which comprises introducing at least one plasmid selected from the group consisting of pCPC901, pCPC902, and pCPC903 into a host microorganism, culturing said microorganism containing the plasmid in a suitable medium, and isolating the pullulanase enzyme produced by the cultured microorganism.

Figure 1:
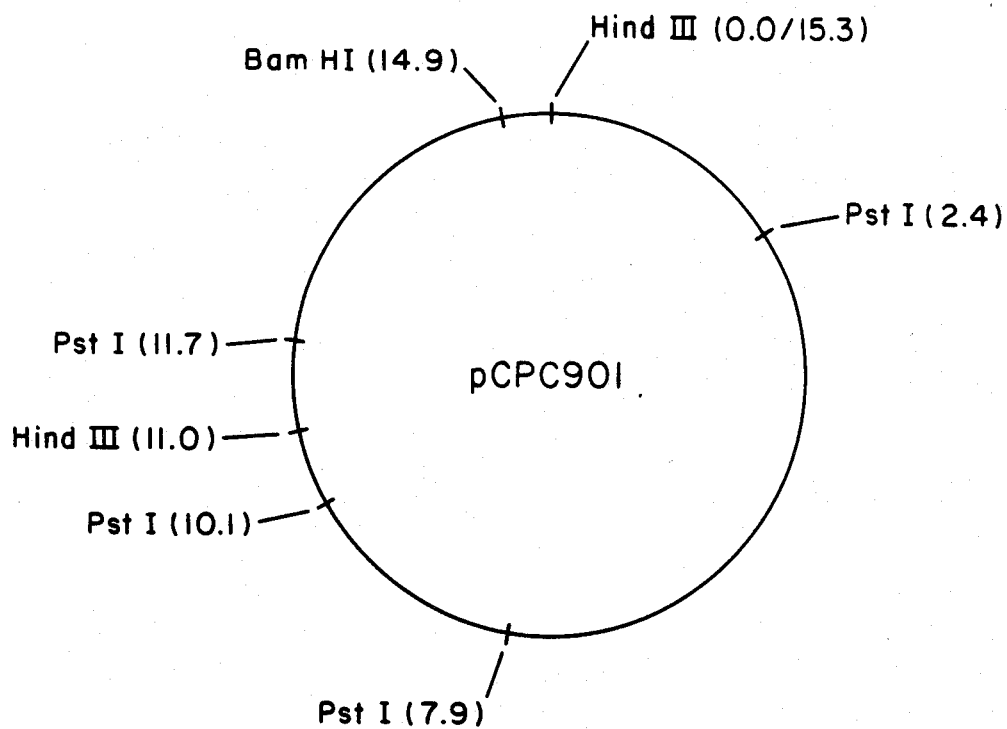
FIGS. 1 to 3 depict the restriction endonuclease cleavage maps for the plasmids: pCPC901, pCPC902, and pCPC903, respectively. The maps are constructed on the basis of the plasmids having the molecular weights in kilobases as given in the figures. The map positions of the various restriction sites are given relative to one restriction site arbitrarily positioned at 0 kb. The restriction endonuclease abbreviations are as follows.

Acc I is an enzyme from *Acinetobacter calcoaceticus*.
Bam HI is an enzyme from *Bacillus amyloliquefaciensH*.
Bgl II is an enzyme from *Bacillus globigii*.
Hind III is an enzyme from *Haemophilus influenzae*.
Kpn I is an enzyme from *Klebsiella pneumonia*.
Pst I is an enzyme from *Providencia stuartii*.
Taq I is an enzyme from *Thermus aquaticus*.

DETAILED DESCRIPTION OF THE INVENTION

Plasmid pCPC901 was constructed using a DNA fragment containing genetic material coding for the production of a pullulanase enzyme. This DNA was obtained by a partial digest of the total DNA produced by the microorganism, *T. brockii*. The method of growing *T. brockii* and its use to produce a pullulanase enzyme are disclosed in a copending patent application Ser. No. 737,309, titled: "Novel Thermostable, Pullulanase Enzyme and Method for Its Production", filed concurrently with this application, the disclosure of which is included herein by reference in its entirety.

Fragments of DNA containing the pullulanase gene were obtained by a partial Hind III digest of the total DNA from *T. brockii*. This DNA was mixed with linear DNA obtained by cutting plasmid pBR322 with Hind III. The mixture of DNA sequences was treated with a ligase using techniques well known in the art. The ligase used for this purpose was a commercially-available T$_4$ DNA ligase.

The plasmids obtained by the ligation reaction were made biologically active by transforming them into host cells of the well-known strain of *E. coli* RR1.

Cells were obtained which grew in the presence of ampicillin at 37° C. Since the *E. coli* cells produce pullulanase intracellularly, it is necessary to lyse the cells before the presence of the enzyme can be detected. Cells of *E. coli* were lysed with a mixture of lysozyme and D-cycloserine. Plasmid DNA was then extracted from a colony that showed both pullulanase activity and resistance to ampicillin. A strain of *E. coli* containing plasmid designated as pCPC901 is available from the American Type Culture Collection as ATCC No. 53116.

Plasmid pCPC901, which has a molecular weight of 15.3 kb, was made smaller by recombining its Hinf partial digest with similar digests of the plasmid, pBR322. The resulting hybrid plasmids were transformed into *E. coli* and the cells were screened for pullulanase activity. One pullulanase-producing colony contained a plasmid of approximately 9.9 kb. This plasmid was designated pCPC902. This plasmid confers ampicillin resistance and the ability to produce pullulanase in host *E. coli* cells.

In order to incorporate the thermostable pullulanase gene into *B. subtilis*, a partial Hinf I digest of plasmid pCPC902 was mixed with a partial Hinf I digest of the plasmid vector, pBD8. The resulting linear DNA was ligated and the resulting hybrid plasmids were transformed into a strain of *B. subtilis*. Transformants were selected for kanamycin resistance and pullulanase activity. One colony, which was a good pullulanase producer, was grown ad its plasmid DNA isolated. This strain produced a plasmid designated as pCPC903, having a molecular weight of approximately 7.5 kb.

Plasmid pCPC903 is capable of being transformed into a *B. subtilis* host, thereby making the host a producer of a thermostable pullulanase enzyme. The plasmid also confers kanamycin resistance to the host. However, the plasmid is stably maintained in the host when the host is grown in a fermentation medium containing no kanamycin.

The following preparations illustrate certain embodiments of the present invention. Unless otherwise stated, all proportions and percentages are provided on the basis of weight.

Plasmid pBR322, T$_4$ DNA ligase, and the restriction endonucleases, unless otherwise noted, used in the following procedures were obtained from the Bethesda Research Laboratories, Bethesda, Maryland. Unless otherwise noted, they were used as described by the supplier. Reagents from the Difco Laboratories, Detroit, Michigan, are designated "Difco".

All strains bearing ATCC numbers are available from the American Type Culture Collection, Rockville, Maryland. Strains containing the plasmids of this invention were deposited in that depository under the provisions of the Budapest Treaty and are available as provided in that Treaty.

Restriction maps given in the figures are obtained by digesting the plasmids with one or more restriction enzymes followed by separation of the resulting pieces of DNA by electrophoresis on agarose gels. The molecular weights of fragments were determined by comparison of the migration rates with those of DNA fragments of known molecular weights. From the molecular weights of the plasmid and the size of the fragments, the restriction endonuclease cleavage maps for the plasmids were determined.

Preparation of Plasmid pCPC901

Total DNA, containing genetic material coding for the thermostable pullulanase, was isolated from cells of a strain of *T. brockii*, ATCC No. 33075, obtained from the American Type Culture Collection, Rockville, Maryland.

The cells were lysed with cold lysozyme solution using standard methods and the cells were centrifuged at 12,000 × g for 20 minutes. Then solid CsCl was added until the solution had a refractive index of 1.395. Ethidium bromide was then added at a concentration of 0.5 µg/ml. The mixture was centrifuged at 45,000 rpm for 24 hours at 20° C. in an ultracentrifuge.

The DNA band was then separated, and the ethidium bromide was removed by extraction with isopropanol saturated with CsCl. The decolorized DNA was dialyzed extensively against a solution containing 10 mM Tris.HCl at pH 7.5 and 1 mM EDTA (ethylenediaminetetraacetate).

A mixture of 20 µg total DNA from *T. brockii*, 100 units of restriction enzyme Hind III, and 144 µl of a solution containing 10 mM Tris.HCl and 1 mM EDTA at pH 8 was incubated at 37° C. for 2 minutes. Then the mixture was held at 70° C. for 1 hour to stop the action of the enzyme. Separately, 3.0 µg of plasmid pBR322 DNA and 5.2 units of Hind III were digested in 40 µl of a similar solution for 30 minutes at 37° C. This mixture was then heated for 1 hour at 70° C. to stop enzyme action.

To a mixture of 70 µl of the above solution of partially-digested *T. brockii* DNA and 10 µl of the above solution of a completely-digested pBR322 DNA was added sufficient water and other ingredients to give 105 µl of a solution containing 10 mM dithiothreitol, 100 mM Tris.HCl (pH 7.6), 10 mM MgCl$_2$, and 0.105 mM adenosine triphosphate. The DNA fragments were joined using 1 unit of T$_4$ DNA ligase. Completeness of the ligation was monitored by analysis on agarose gels.

A culture of *E. coli* RRI, available from the Plasmid Reference Center, Stanford University Medical Center, Stanford, California, was grown in the following LB medium:

|  | g/Liter |
| --- | --- |
| Tryptone | 10.0 |
| Yeast Extract | 5.0 |
| Sodium Chloride | 5.0 |
| Glucose | 1.0 |

The culture was grown in a tube overnight at 37° C. It was then diluted with nine parts of the same medium and incubated at 37° C. for an additional 135 minutes with vigorous agitation. The cells were harvested by centrifugation and washed with cold 0.1 M NaCl solution. The harvested *E. coli* cells were prepared for transformation by the calcium chloride method of Cohen, et al, *Proc. Nat. Acad. Sci.*, U.S.A., 69, 2110–2114 (1972).

The ligated DNA prepared above was transformed into competent cells of *E. coli* RR1. The cells were cultivated on agar plates containing LB medium and ampicillin at a concentration of 100 µg/ml. By this means, cells of *E. coli* containing DNA from the plasmid pBR322 (with ampicillin-resistant genes) were obtained.

The plates were replicated onto plates containing the following pullulan medium:

| Compound | g/Liter |
| --- | --- |
| Peptone | 10.0 |
| Na$_2$HPO$_4$ | 6.0 |
| KH$_2$PO$_4$ | 3.0 |
| NaCl | 0.5 |
| NH$_4$Cl | 1.0 |
| Yeast Extract | 1.0 |
| Pullulan | 3.0 |
| Agar | 15.0 |

After the plates have been incubated at 37° C. for 5 hours, they were overlayed with a 1% agar solution containing 0.3% pullulan and 0.05% D-cycloserine. The overlayed plates were incubated at 37° C. overnight and then for 5 hours at 60° C. to accelerate pullulan hydrolysis. Cold 0° C.) absolute ethanol was poured over the surface of the agar to precipitate the pullulan in this medium. One spot was observed where pullulan was hydrolyzed to a clear zone indicating the colony contained cloned pullulanase gene. The corresponding colony was located on the original plate. Cells of this pullulanase-producing colony were grown on the LB-ampicillin (100 µg/ml) agar plates.

The recombinant plasmid DNA was extracted from the pullulanase-producing cells. The general method of Clewell, *J. Bacteriology*, 110, 667–676 (1972), was used with the following changes. The culture was grown in a 1-liter Hinton flask containing 250 ml of the medium used to grow *E. coli* to which was added 100 µg/ml of ampicillin. The culture was incubated at 37° C. with 300 rpm stirring and no chloramphenicol was added for amplification. The cells were collected by centrifugation and frozen at −35° C. prior to lysis. The lysed cells were not centrifuged but instead the entire mixture was subjected to the cesium chloride-ethidium bromide DNA purification procedure described above. The mixture was first centrifuged at 5000× g for 5 minutes and the cell debris was removed from the top of the gradient before the remaining mixture was separated by ultracentrifugation. A plasmid designated as pCPC901 was isolated. It has a molecular weight of approximately 15.3 kb. Its restriction endonuclease cleavage map is given in FIG. 1. A biologically pure culture of *E. coli* containing plasmid pCPC901 is available as ATCC No. 53116.

PREPARATION OF PLASMID pCPC902

To facilitate cloning of the pullulanase gene into *B. subtilis*, plasmid pCPC901 was partially digested with Hinf I, plasmid pBR322 was similarly cut, and the resulting pieces were circularized with T$_4$ DNA ligase. The resulting plasmids were transformed into *E. coli* RR1 by the same method as used for the preparation of pCPC901. Colonies with ampicillin resistance which produced pullulanase were again selected. A recombinant plasmid, pCPC902, isolated from one colony, was analyzed by agarose gel electrophoresis. This is a 9.9 kb plasmid with the endonuclease restriction map given in FIG. 2. A biologically pure culture of *E. coli* containing pCPC902 is available as ATCC No. 53114.

Preparation of Plasmid pCPC903

A portion of plasmid pCPC902 was combined with the plasmid vector pBD8, available from the American Type Culture Collection, Rockville, Maryland. To accomplish this, both plasmids were partially digested with the restriction endonuclease Hinf I as follows:

A 5-µg portion of each DNA was incubated with 5 units of Hinf I at 37° C. After 2, 5, 10, and 15 minutes, aliquots were heated at 70° C. for 20 minutes to stop enzyme action. The DNA from each sample was then ethanol precipitated in 0.5 M NaCl, dried, and resuspended in 100 µl of 20 mM Tris, pH 7.5, 10 mM dithiothreitol, 5 mM MgCl$_2$, 0.5 mM ATP. Fragments were ligated with 1 unit of T$_4$ DNA ligase at 5°–10° C. overnight. The recombinants were then ethanol precipitated, dried, and stored.

The combined DNA was transformed into an amylase-negative strain of *B. subtilis*, B1-20 (metB5, amyE, sacA321). This strain is available from the American Type Culture Collection as ATCC No. 39706.

To make competent cells, B1-20 was grown at 37° C. overnight on Difco Tryptose Blood Agar Base (TBAB) plates. Cells from the plates were then suspended in a small amount of growth medium and used to inoculate about 60 ml of additional growth medium in a 500-ml Erlenmeyer flask. The mixture was grown at 33°–37° C. with shaking at 250–270 rpm. The growth medium contained the following ingredients: 0.5% glucose, 0.6% KH$_2$PO$_4$, 1.4% K$_2$HPO$_4$, 0.1% sodium citrate, 0.2% (NH$_4$)$_2$SO$_4$, 0.01% MgSO$_4$, 0.02% Casamino acids (Difco), 0.1% yeast extract (Difco) and 0.02% L-tryptophan. Growth was monitored by following optical density at 620 nm. When cultures reached the transition between log and stationary growth (change in optical density less than 5% in 15 minutes), they were diluted with 2 volumes of transformation medium. The medium had the same composition as the growth medium except that it contained an additional 2% of 0.1 M MgCl$_2$ and 1% of 0.05 M CaCl$_2$. Dilution into prewarmed transformation medium at 33°–37° C. was performed. The mixture was incubated at this temperature for 90 minutes with shaking at 250–270 rpm. Five minutes prior to the end of the incubation period sterile 20 mM ethylene glycol-bis(beta-aminoethyl ether)-N,N,N',N'-tetraacetic acid was added to give a final concentration of 1 mM.

Transformation was accomplished by mixing 1–10 µl of DNA (0.1–1 µg) isolated as described above with 0.5 ml of competent cells of Strain B1-20 described above. The mixture was incubated at 37° C. for 90 minutes with shaking at 250 rpm. The cultures were plated on TBAB-kanamycin (10 µg/ml) and incubated overnight at 37° C. Kanamycin-resistant colonies were replica plated on agar plates containing Difco tryptic soy medium and 1.5% pullulan-reactive red (a mixture of pullulan and reactive red dye). Plates were incubated for 16 hours at 37° C. and then 8 hours at 60° C. Clear zones around colonies indicated which kanamycin-resistant transformants were pullulanase producers.

One colony was selected which maintained its ability to produce pullulanase when grown at 37° C. in the absence of kanamycin. The plasmid isolated from this colony was designated as pCPC903. It is a 7.5 kb plasmid with the restriction endonuclease cleavage map given in FIG. 3. The plasmid was readily transformed into competent cells of B. subtilis, Strain B1-20. A biologically pure culture of this strain containing plasmid pCPC903 is available as ATCC No. 53115.

Preparation of Pullulanase

Extracellular pullulanase enzyme preparations were prepared from the strain of B. subtilis, ATCC No. 53115, containing plasmid pCPC903.

To prepare working stock cultures, the cells were grown at 37° C. for 24 hours in 10 ml of tryptic soy broth (Difco) containing 0.5% dextrose and 15 μg/ml of kanamycin. The culture was mixed with an equal volume of 50% glycerol and stored at −70° C.

For production of enzyme, an inoculum was prepared using a stock culture to grow cells on Difco tryptic soy agar plates containing 0.5% dextrose and 10 μg/ml kanamycin. The growth was continued for 16 hours at 38° C. A colony from the plates was used to inoculate 100 ml of half-strength growth medium containing 10 μg/ml of kanamycin.

| Growth Medium | |
| --- | --- |
| | Weight, % |
| Dextrose | 2.5 |
| Soyafluff 200W[a] | 6.0 |
| Amberex[b] | 1.0 |
| (NH$_4$)$_2$HPO$_4$ | 0.6 |
| CaCl$_2$.2H$_2$O | 0.06 |
| MgSO$_4$.7H$_2$O | 0.10 |
| KH$_2$PO$_4$ | 0.13 |
| MnCl$_2$.4H$_2$O | 0.50 |
| FeCl$_2$.4H$_2$O | 0.001 |

[a] A soy protein, available from Central Soya, Fort Wayne, Ind.
[b] An autolyzed yeast extract, available from Amber Laboratories, Milwaukee, Wis.

The mixture was shaken in a 500-ml triple-baffled Belco flask at 250 rpm and 38° C. for 24 hours, then 5 ml of this inoculum was added to 100 ml of growth medium containing the kanamycin. This mixture was again shaken for 6 hours at 38° C. Then a 10-ml portion was used to inoculate 200 ml of growth medium in 1-liter baffled flasks. These flasks were shaken at 250 rpm while being incubated at 38° C. for 65 hours. Cells were removed from the fermentation mixture by centrifugation to give a clear supernatant containing the enzyme in solution. The yield of enzyme varied from 1.0 to 1.6 units per ml of fermentation broth.

Thus, there has been provided, in accordance with this invention, essentially pure plasmids containing genetic sequences coding for a thermostable pullulanase enzyme. Also provided are strains of E. coli and B. subtilis containing these plasmids and a process for their use to produce the thermostable pullulanse enzyme.

While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

Figure 2:
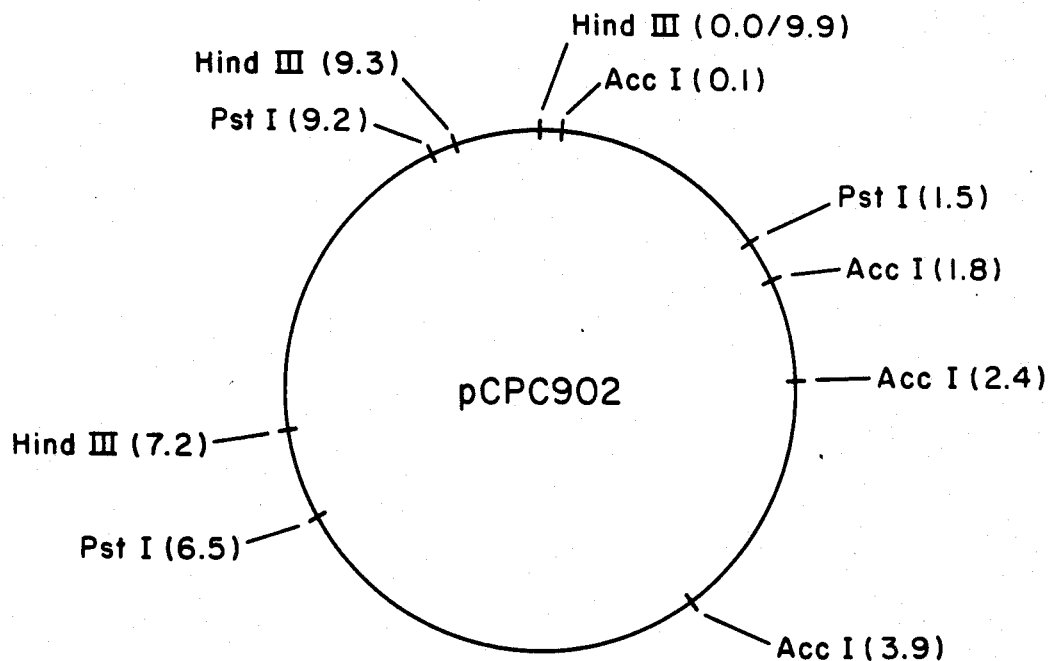
Figure 3:
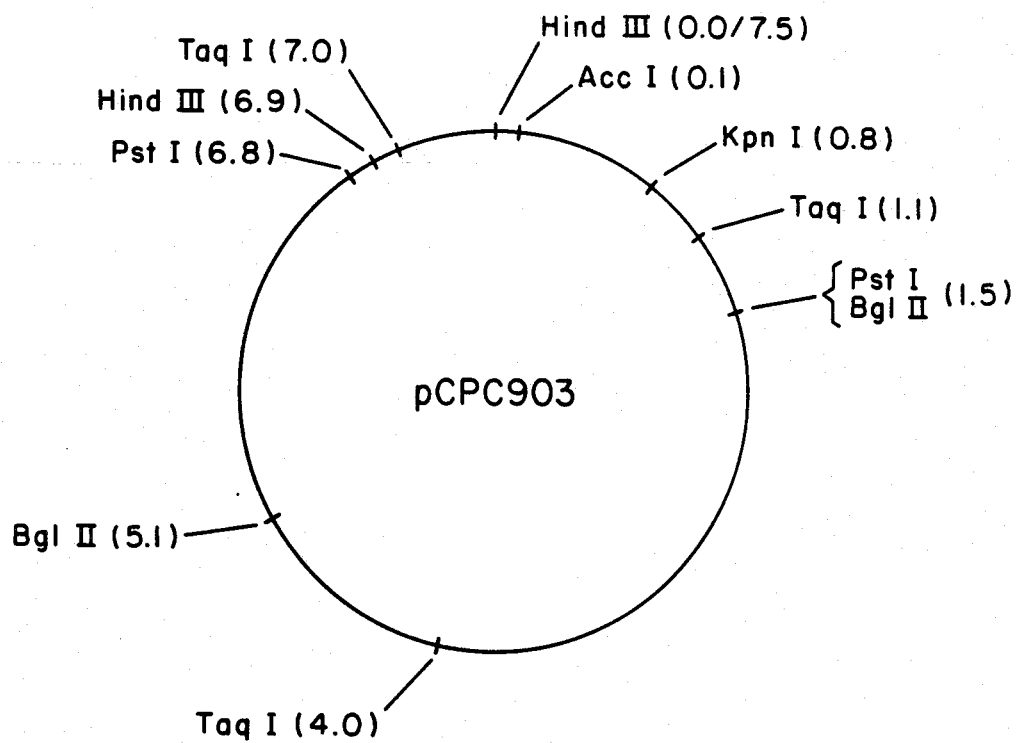

What is claimed is:

1. An essentially pure plasmid, having a genetic sequence coding for a thermostable pullulanase enzyme, selected from the group: pCPC901, having a molecular weight of approximately 15.3 kb and a restriction endonuclease cleavage map as shown in FIG. 1; pCPC902, having a molecular weight of approximately 9.9 kb and a restriction endonuclease cleavage map as shown in FIG. 2; and pCPC903, having a molecular weight of approximately 7.5 kb and a restriction endonuclease cleavage map as shown in FIG. 3.

2. A strain of B. subtilis containing the plasmid, pCPC903, capable of growing at a temperature of 37° C. for about 32 hours without loss of the plasmid, and capable of producing an extracellular thermostable pullulanase enzyme.

3. The strain of B. subtilis of claim 2 having ATCC No. 53115.

4. A strain of E. coli, capable of growing in a medium containing ampicillin at a concentration of 100 μg/ml and containing a plasmid which includes a thermostable pullulanase coding gene, said plasmid selected from a group consisting of pCPC901 and pCPC902.

5. The strain of E. coli of claim 4 selected from the group consisting of ATCC No. 53114 and ATCC No. 53116.

6. The process of preparing a thermostable pullulanase enzyme which comprises the steps of:
   (a) introducing at least one plasmid of claim 1 into a host microorganism;
   (b) culturing said microorganism containing the plasmid in a suitable medium; and
   (c) isolating the pullulanase enzyme produced by the cultured microorganism.

7. The process of claim 6 wherein the plasmid is pCPC903, and the microorganism containing the plasmid is the strain of B. subtilis, ATCC No. 53115.

* * * * *